US010383972B2

(12) United States Patent
Gu et al.

(10) Patent No.: US 10,383,972 B2
(45) Date of Patent: Aug. 20, 2019

(54) HOT MELT WETNESS INDICATOR COMPOSITION THAT INCLUDES A LEUCO DYE, AND ARTICLES INCLUDING THE SAME

(71) Applicant: H.B. Fuller Company, St. Paul, MN (US)

(72) Inventors: Yuanyan Gu, St Paul, MN (US); Ryan T. Gleason, Fort Worth, TX (US); Michael C. Krzoska, Hugo, MN (US); Steven R. Vaughan, Lake Elmo, MN (US); Carlos Briseno, St. Paul, MN (US); Kevin P. Davis, Woodbury, MN (US)

(73) Assignee: H.B. Fuller Company, St. Paul, MN (US)

( * ) Notice: Subject to any disclaimer, the term of this patent is extended or adjusted under 35 U.S.C. 154(b) by 631 days.

(21) Appl. No.: 15/088,896

(22) Filed: Apr. 1, 2016

(65) Prior Publication Data

US 2016/0287742 A1 Oct. 6, 2016

Related U.S. Application Data

(60) Provisional application No. 62/254,300, filed on Nov. 12, 2015, provisional application No. 62/142,736, filed on Apr. 3, 2015.

(51) Int. Cl.

| | |
|---|---|
| ***A61F 13/42*** | (2006.01) |
| ***A61L 15/56*** | (2006.01) |
| ***A61L 15/20*** | (2006.01) |
| ***A61L 15/22*** | (2006.01) |
| ***A61L 15/24*** | (2006.01) |
| ***A61L 15/34*** | (2006.01) |

(52) U.S. Cl.

CPC .............. *A61L 15/56* (2013.01); *A61F 13/42* (2013.01); *A61L 15/20* (2013.01); *A61L 15/225* (2013.01); *A61L 15/24* (2013.01); *A61L 15/34* (2013.01); *A61F 2013/422* (2013.01); *A61F 2013/426* (2013.01); *A61F 2013/427* (2013.01)

(58) Field of Classification Search

CPC ................ A61F 13/42; A61F 2013/422; A61F 2013/426; A61F 2013/427; A61F 2013/429; A61L 15/56; C09J 2201/61

See application file for complete search history.

(56) References Cited

U.S. PATENT DOCUMENTS

| | | | |
|---|---|---|---|
| 2,537,124 | A | 1/1946 | Earle et al. |
| 4,231,370 | A | 11/1980 | Mroz et al. |
| 4,681,576 | A | 7/1987 | Colon et al. |
| 4,743,238 | A | 5/1988 | Colon et al. |
| 4,895,567 | A | 1/1990 | Colon et al. |
| 6,772,708 | B2 | 8/2004 | Klofta et al. |
| 6,904,865 | B2 | 6/2005 | Klofta et al. |
| 7,159,532 | B2 | 1/2007 | Klofta et al. |
| 7,307,231 | B2 | 12/2007 | Matsumoto et al. |
| 7,495,894 | B2 | 2/2009 | Yu et al. |
| 8,061,292 | B2 | 11/2011 | Ahmed et al. |
| 8,080,704 | B2 | 12/2011 | Uchida et al. |
| 8,557,894 | B2 | 10/2013 | Gil et al. |
| 8,697,003 | B2 | 4/2014 | Song |
| 8,754,005 | B2 | 6/2014 | Gil et al. |
| 8,784,689 | B2 | 7/2014 | Song |
| 8,911,681 | B2 | 12/2014 | Song et al. |
| 2007/0108032 | A1 | 5/2007 | Matsumoto et al. |
| 2007/0197986 | A1 | 8/2007 | Matsui |
| 2009/0017299 | A1* | 1/2009 | Shimbo .................. B41M 5/502 428/355 N |
| 2009/0326494 | A1 | 12/2009 | Uchida et al. |
| 2010/0244682 | A1 | 9/2010 | Lee et al. |
| 2010/0264369 | A1 | 10/2010 | Zhang |
| 2011/0015063 | A1 | 1/2011 | Gil et al. |
| 2011/0015597 | A1 | 1/2011 | Gil et al. |
| 2011/0015599 | A1 | 1/2011 | Song et al. |
| 2011/0152805 | A1 | 6/2011 | Gil |
| 2011/0223389 | A1 | 9/2011 | Lin et al. |
| 2012/0133608 | A1 | 5/2012 | Chen |
| 2012/0143160 | A1 | 6/2012 | Song |
| 2012/0150134 | A1* | 6/2012 | Wei ......................... A61L 15/56 604/361 |
| 2012/0308787 | A1* | 12/2012 | Kozee ...................... B41J 3/407 428/195.1 |
| 2013/0141345 | A1 | 6/2013 | Wng |
| 2014/0015063 | A1 | 1/2014 | Yang et al. |
| 2014/0078413 | A1 | 3/2014 | Yu et al. |
| 2014/0207095 | A1 | 7/2014 | Song |
| 2014/0363354 | A1 | 12/2014 | Phillips et al. |
| 2015/0094676 | A1 | 4/2015 | Klofta |
| 2016/0303275 | A1 | 10/2016 | Laveeta et al. |

FOREIGN PATENT DOCUMENTS

| | | | |
|---|---|---|---|
| EP | 2 067 458 | A1 | 6/2009 |
| WO | WO 02/36177 | A2 | 5/2002 |
| WO | WO-2007/010385 | A1 | 1/2007 |
| WO | WO 2013/070674 | | 5/2013 |

OTHER PUBLICATIONS

Gohain et al., "Premicellar and micelle formation behavior of aqueous anionic surfactants in the presence of triphenyitmethane dyes: protonation of dye in ion pair micelles," *J. Phys. Org. Chem.*, 2010, pp. 211-219, vol. 23, John Wiley & Sons., Ltd.

* cited by examiner

*Primary Examiner* — Catharine L Anderson
(74) *Attorney, Agent, or Firm* — Kirsten Stone; Allison Johnson

(57) ABSTRACT

A hot melt wetness indicator composition that includes a water insoluble thermoplastic polymer, an anionic surfactant, a leuco dye, and a component selected from the group consisting of acid, rosin-based tackifying agent, plasticizer and combinations thereof, and is homogeneous is disclosed. The hot melt wetness indicator composition exhibits a color change after contact with water.

19 Claims, No Drawings

HOT MELT WETNESS INDICATOR COMPOSITION THAT INCLUDES A LEUCO DYE, AND ARTICLES INCLUDING THE SAME

CROSS REFERENCE TO RELATED APPLICATIONS

This application claims the benefit of U.S. Provisional Application No. 62/142,736, filed Apr. 3, 2015, and U.S. Provisional Application No. 62/254,300 filed Nov. 12, 2015, both of which are incorporated herein.

BACKGROUND

The invention is directed to formulating a composition that includes a leuco dye and that changes color after exposure to water.

Hot melt wetness indicator compositions are used to provide a visual indication of a change in the state of wetness of the composition and are frequently used in diapers to provide a visual indication that a diaper is in need of changing. Hot melt wetness indicator compositions are often formed with a pH sensitive colorant such as bromocresol green or bromophenol blue. These colorants turn from a first color, such as yellow, to a second color, such as green, as a result of a change in pH.

Leuco dyes have also been used in volatile organic solvent-based color changing compositions. Leuco dyes are dye molecules that have two forms, one of which is colorless and one of which is colored. Leuco dyes are often supplied as solid particles.

Hot melt applicators typically require compositions that are free of particulate in order to properly dispense a hot melt composition. When particles are present in a hot melt composition, the particles can clog the application equipment that is typically used to apply such compositions, can interfere with the definition of the pattern formed when the composition is applied on a substrate, and tend to settle to the bottom of the "pot" or vessel that holds the bulk of the hot melt composition prior to application.

It would be desirable to have a hot melt wetness indicator composition that provides a distinct color change when contacted with an aqueous liquid such as water, urine or saline, and that can be applied using existing hot melt applicator equipment.

SUMMARY

In one aspect, the invention features a hot melt wetness indicator composition that includes water insoluble thermoplastic polymer, anionic surfactant, leuco dye, and a component selected from the group consisting of acid, rosin-based tackifying agent, and combinations thereof, the hot melt wetness indicator composition being homogeneous and exhibiting a color change after contact with water. In some embodiments, the composition further includes plasticizer. In other embodiments, the composition further includes at least 10% by weight plasticizer. In another embodiment, the composition includes dissolved leuco dye particles.

In another aspect, the invention features a hot melt wetness indicator composition that includes at least 5% by weight water insoluble thermoplastic polymer, at least 3% by weight anionic surfactant, leuco dye, and at least 10% by weight of a component selected from the group consisting of acid, rosin-based tackifying agent, plasticizer, and combinations thereof, the hot melt wetness indicator composition being homogeneous and exhibiting a color change after contact with water. In one embodiment, the composition includes at least 5% by weight rosin-based tackifying agent. In other embodiments, the composition includes from about 10% by weight to no greater than 60% by weight rosin-based tackifying agent.

In another embodiment, the composition includes from about 10% by weight to no greater than 60% by weight acid, rosin-based tackifying agent, or a combination thereof, where the acid includes a rosin acid and the rosin-based tackifying agent is different from the rosin acid. In one embodiment, the composition includes at least 20% by weight acid, rosin-based tackifying agent, or a combination thereof, the rosin-based tackifying agent being different from the acid.

In some embodiments, the composition includes at least 2% by weight of the acid. In other embodiments, the composition includes at least 2% by weight rosin acid.

In another embodiment, the composition includes at least 5% by weight plasticizer.

In other embodiments, the composition includes at least two components selected from the group consisting of the acid, the rosin-based tackifying agent, and the plasticizer, the rosin-based tackifying agent being different from the acid.

In some embodiments, the composition includes the plasticizer and the rosin-based tackifying agent.

In other embodiments, the composition includes at least about 15% by weight rosin-based tackifying agent, plasticizer, or a combination thereof. In another embodiment, the composition includes at least about 20% by weight rosin-based tackifying agent, plasticizer, or a combination thereof.

In some embodiments, the composition includes the acid and the plasticizer. In other embodiments, the composition includes at least about 15% by weight plasticizer, acid, or a combination thereof. In other embodiments, the composition includes at least about 20% by weight plasticizer, acid, or a combination thereof.

In other embodiments, the composition includes acid, plasticizer, and rosin-based tackifying agent, the rosin-based tackifying agent being different from the acid. In one embodiment, the composition includes a first rosin-based tackifying agent and a second rosin-based tackifying agent, the first rosin-based tackifying agent being different from the second rosin-based tackifying agent. In some embodiments, the acid, plasticizer, and rosin-based tackifying agent comprise at least 10% by weight of the composition. In other embodiments, the acid, plasticizer, and rosin-based tackifying agent comprise at least 15% by weight of the composition. In other embodiments, the acid, plasticizer, and rosin-based tackifying agent comprise at least about 20% by weight of the composition.

In one embodiment, the composition includes from about 10% by weight to no greater than 90% by weight of the water insoluble thermoplastic polymer. In another embodiment, the composition includes from about 10% by weight to no greater than 65% by weight of the water insoluble thermoplastic polymer. In another embodiment, the composition includes from about 15% by weight to no greater than 65% by weight of the water insoluble thermoplastic polymer. In some embodiments, the water insoluble thermoplastic polymer is free of carboxylic acid groups.

In one embodiment, the composition exhibits a viscosity of no greater than 30,000 cP at 110° C. In other embodiments, the composition exhibits a viscosity of from about 1000 cP to no greater than about 20,000 cP at 110° C.

In another embodiment, the composition includes from about 5% by weight to no greater than 30% by weight anionic surfactant.

In other embodiments, the composition includes leuco dye particles that are dissolved in the composition.

In one embodiment, the composition remains homogeneous when maintained at 110° C. for 1 day. In some embodiments, the composition remains homogeneous when maintained at 110° C. for 2 days. In other embodiments, the composition remains homogeneous when maintained at 110° C. for 3 days.

In other embodiments, the composition exhibits no change in color when tested according to the Humidity Resistance test method for a period of 24 hours.

In another embodiment, the composition includes from 5% by weight to 90% by weight water insoluble thermoplastic polymer, at least 3% by weight anionic surfactant, leuco dye, and from 10% by weight to about 70% by weight of a component selected from the group consisting of acid, rosin-based tackifying agent, plasticizer, and combinations thereof. In other embodiments, the composition includes from 5% by weight to 90% by weight water insoluble thermoplastic polymer, at least 3% by weight anionic surfactant, leuco dye, and from 10% by weight to about 65% by weight of a component selected from the group consisting of acid, rosin-based tackifying agent, plasticizer, and combinations thereof. In other embodiments, the composition includes from 5% by weight to 90% by weight water insoluble thermoplastic polymer, at least 3% by weight anionic surfactant, leuco dye, and from 15% by weight to about 55% by weight of a component selected from the group consisting of acid, rosin-based tackifying agent, plasticizer, and combinations thereof. In another embodiment, the composition includes from 5% by weight to 80% by weight water insoluble thermoplastic polymer comprising at least one of an elastomeric block copolymer and an olefin polymer, at least 3% by weight anionic surfactant, leuco dye, and from 15% by weight to about 55% by weight of a component selected from the group consisting of acid, rosin-based tackifying agent, plasticizer, and combinations thereof.

In some embodiments, the composition includes a colorant other than the leuco dye. In other embodiments the composition includes a colorant other than the leuco dye and the composition exhibits a color exhibited by a protonated form of the leuco dye when the composition is contacted with water. In one embodiment, the composition includes a colorant other than the leuco dye and the composition exhibits a blue color when contacted with water. In some embodiments, the composition includes a colorant and exhibits a first color, and, when the composition is contacted with water, the composition exhibits a second color, the second color being different from the first color.

In another aspect, the invention features a method of making a wetness indicator composition, the method including combining with heating and mixing a leuco dye, anionic surfactant, and a component selected from the group consisting of a rosin-based tackifying agent, acid, plasticizer, and combinations thereof, to form a molten composition, and subsequently adding a water insoluble thermoplastic polymer to the molten composition. In some embodiments, the leuco dye is in the form of particles prior to the combining. In other embodiments, the molten composition is homogeneous prior to adding the water insoluble thermoplastic polymer. In one embodiment, the method further includes adding at least one additional component to the molten composition. In another embodiment, the method further includes forming a homogeneous composition.

In other aspects, the invention features a hot melt wetness indicator composition that includes at least 10% by weight of a water insoluble thermoplastic polymer that is free of carboxyl groups, anionic surfactant, leuco dye, and a component selected from the group consisting of an acid, a rosin-based tackifying agent, a plasticizer, and combinations thereof, the hot melt wetness indicator composition being homogeneous and exhibiting a color change after contact with water.

Other features and advantages will be apparent from the following description of the preferred embodiments and from the claims.

Glossary

In reference to the invention, these terms have the meanings set forth below:

The term "leuco dye" means a molecule that can exhibit two forms and that can transition from a colorless form to a colored form.

The term "homogeneous composition" means a composition that is free of visible phase separation as determined by viewing the composition in the molten state with the naked eye.

DETAILED DESCRIPTION

The hot melt wetness indicator composition includes a water insoluble thermoplastic polymer, anionic surfactant, a leuco dye, and at least one of acid, rosin-based tackifying agent, and plasticizer, exhibits a color change after contact with an aqueous composition (e.g., water, urine, saline, and combinations thereof), and is solid at room temperature. The color change may be in the form of a change in hue, a change in lightness, a change in colorfulness, or a combination thereof. When contacted with water, the wetness indicator composition changes color after a relatively short period of time. The wetness indicator composition preferably changes color in no greater than 5 minutes, no greater than about 3 minutes, no greater than about 2 minutes, or even no greater than about 1 minute when tested according to the Color Change Test Method. The wetness indicator composition preferably exhibits a color change that is uniform over the area of composition that has been contacted with water.

The wetness indicator composition exhibits a viscosity of no greater than 50,000 cP, no greater than 30,000 cP, at least about 1000 cP, at least about 2000 cP, from about 2000 cP to about 20,000 cP, from about 3000 cP to about 15,000 cP, or even from about 5000 cP to about 15,000 cP at 110° C.

The wetness indicator composition preferably is homogeneous. The wetness indicator composition also preferably is free of gelling and remains homogeneous when maintained at a temperature of 110° C. for a period of at least 1 day, at least 2 days, or even at least 4 days.

The wetness indicator composition also exhibits good humidity resistance. The wetness indicator composition preferably exhibits no change in color after at least 24 hours, at least 3 days, or even at least 4 days when tested according to the Humidity Resistance Test Method.

Water Insoluble Thermoplastic Polymer

Useful water insoluble thermoplastic polymers include, e.g., homopolymers, copolymers, terpolymers, and higher order thermoplastic polymers. Suitable classes of thermoplastic polymers include, e.g., olefin polymer (e.g., olefin homopolymers, copolymers and higher order polymers (e.g., ethylene vinyl acetate, polyolefins (e.g., polyethylene, polypropylene, metallocene-catalyzed polyolefins, and combinations thereof)), and combinations thereof; acrylates (e.g., alkyl acrylates and methacrylates (e.g., ethyl acrylate, ethyl methacrylate, ethyl n-butyl acrylate, butyl acrylate, butyl methacrylate, and combinations thereof); elastomers (e.g., elastomeric block copolymers (e.g., styrene-butadiene-styrene, styrene-isoprene-styrene, styrene-ethylene/butylene-styrene, and styrene-ethylene/propylene-styrene), elastomeric polyolefins, and combinations thereof); thermoplastic polyesters; thermoplastic polyamides; thermoplastic polyurethanes; and combinations thereof. The water insoluble polymer optionally is free of carboxylic acid groups.

Useful commercially available vinyl copolymers include, e.g., ESCORENE AD2528 ethylene vinyl acetate copolymers from ExxonMobil Chemical Company (Houston, Tex.), and ATEVA 2850 ethylene vinyl acetate copolymers from Celanese Corp. (Irving, Tex.).

Useful commercially available elastomeric block copolymers are available under a variety of trade designations including, e.g., KRATON D and G block copolymers from Kraton Polymers LLC (Houston, Tex.) including KRATON G 1650, 1652, and 1657 styrene-ethylene/butylene-styrene block copolymers, VECTOR block copolymers from TSRC/Dexco Investment Corp. (Houston, Tex.) including VECTOR 6241A styrene-butadiene-styrene block copolymer, EUROPRENE block copolymers from Versalis SPA Corp. (Milan, Italy) including EUROPRENE SOL TH 2311 styrene-ethylene/butylene-styrene, and SOLPRENE 411 styrene-butadiene-styrene block copolymer Dynasol Synthetic Rubber Co. Ltd. (Houston, Tex.).

Useful commercially available polyolefins are available under a variety of trade designations including, e.g., REXTAC propylene-based polymers, ethylene-propylene copolymers, and butene-propylene copolymers available from Rextac LLC (Odessa, Tex.), VESTOPLAST alpha-olefin copolymers available from Evonik Degussa GMBH LLC (Germany), AFFINITY and ENGAGE linear ethylene alpha-olefin copolymers available from Dow Chemical Company (Midland, Mich.), and VISTAMAXX propylene-based polymers from Exxon Mobil Corporation (Irving, Tex.).

The composition includes at least 5% by weight, at least about 10% by weight, at least about 25% by weight, at least about 35% by weight, no greater than about 90% by weight, no greater than about 80% by weight, or even no greater than about 65% by weight water insoluble polymer.

The composition includes from about 0% by weight to about 90% by weight, at least 25% by weight, from about 25% by weight to about 90% by weight, from about 35% by weight to about 80% by weight, or even from about 40% by weight to about 65% by weight water insoluble thermoplastic olefin polymer.

The composition includes from about 0% by weight to about 30% by weight, at least 5% by weight, from about 5% by weight to about 30% by weight, from about 5% by weight to about 25% by weight, or even from about 10% by weight to about 20% by weight water insoluble thermoplastic elastomer.

Anionic Surfactant

Useful classes of anionic surfactants include, e.g., sulfates, sulfonates, phosphates, and carboxylates. Suitable examples of anionic surfactants include, e.g., C8-C60 alkyl sulfonates, alkyl benzene sulfonates, alkyl sulfates (e.g., ammonium lauryl sulfate and sodium lauryl sulfate), alkyl ether sulfates (e.g., sodium laureth sulfate and sodium myreth sulfate), sulfosuccinates, alkylphenol sulfates, alkyl carboxylates (e.g., sodium stearate), C8-C60 alkyl ethoxylate sulfonates, and combinations thereof.

Useful commercially available surfactants are available under a variety of trade designations including, e.g., RHODACAL DS-10 sodium dodecylbenzene sulfonate from Solvay Americas, Inc. (Houston, Tex.), NACCONOL 90G sodium dodecylbenzene sulfonate from Stepan Company (Northfield, Ill.), RHODAPON UB sodium dodecylsulfonate available from Solvay America, Inc., and CALSOFT alkyl sulfonates from Pilot Chemical Company (Cincinnati, Ohio).

The composition preferably includes at least 3% by weight, at least 5% by weight, at least 8% by weight, at least 10% by weight, from about 5% by weight to about 30% by weight, 5% by weight to about 25% by weight, or even from about 5% by weight to about 20% by weight anionic surfactant.

Leuco Dye

The composition can include any suitable leuco dye. Useful classes of leuco dyes include, e.g., phthalide leuco dyes, triarylmethane leuco dyes, fluoran leuco dyes, and combinations thereof. Useful triarylmethane-based leuco dyes include, e.g. 3,3-bis(p-dimethylaminophenyl)-6-dimethylaminophthalide, 3,3-bis(p-dimethylaminophenyl) phthalide, 3-(p-dimethylaminophenyl)-3-(1,2-dimethylindol-3-yl)phthalide, 3-(p-dimethylaminophenyl)-3-(2-methylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-p-dimethylaminophenyl-3-(1-methylpyrrol-3-yl)-6-dimethylaminophthalide, and combinations thereof.

Useful diphenylmethane-based leuco dyes include, e.g., 4,4'-bisdimethylaminobenzhydryl benzyl ether, N-halophenylleucoauramine, N-2,4,5-trichlorophenyl-leucoauramine, and combinations thereof.

Useful lactam-based leuco dyes include, e.g., rhodamine-B-anilinolactam, rhodamine-(p-nitroanilino)lactam, rhodamine-(o-chloroanilino)lactam, and combinations thereof.

Useful fluoran-based leuco dyes include, e.g., 3-dimethylamino-7-methoxyfluoran, 3-diethylamino-6-methoxyfluoran, 3-di-ethylamino-7-methoxyfluoran, 3-diethylamino-7-chlorofluoran, 3-diethylamino-6-methyl-7-chlorofluoran, 3-di-ethylamino-6,7-dimethylfluoran, 3-(N-ethyl-p-toluidino)-7-methylfluoran, 3-diethylamino-7-(N-acetyl-N-methylamino)fluoran, fluoran, 3-diethylamino-7-(N-methylamino)fluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino) fluoran, 3-diethylamino-6-methyl-7-phenylaminofluoran, 3-dibutylamino-6-methyl-7-phenylaminofluoran, 3-diethylamino-7-(2-carbomethoxyphenylamino) fluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-(2,4-dimethylamino)fluoran, 3-diethylamino-7-(o-chlorophenylamino)fluoran, 3-dibutylamino-7-(o-chlorophenylamino)fluoran, 3-pyrrolidino-6-methyl-7-(p-butylphenylamino) fluoran, 3-(N-methyl-N-n-amylamino)-6-methyl-7-phenylaminofluoran, 3-(N-ethyl-N-n-amylamino)-6-methyl-7-phenylaminofluoran, 3-(N-ethyl-N-isoamylamino)-6-methyl-7-phenylaminofuluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-.beta.-ethylhexylamino)-6-methyl-7-phenylaminofluoran, and combinations thereof.

Useful leuco dyes include leuco dyes that are solid at room temperature including, e.g., leuco dyes in the form of particles. Leuco dye particles preferably are dissolved in the wetness indicator composition such that no particles are visible when the composition in the molten state is viewed with the naked eye.

Useful commercially available leuco dyes include the leuco dyes available under the trade designation N-102 from ESCO Co. LLC. (Muskegon, Mich.), Crystal Violet Lactone (CVL) from Shanghai Lucky B & C Technology Co. Ltd. (Shanghai, China), and BLUE 230 from Nagase Inc. (Japan).

The composition includes from about 0.1% by weight to about 10% by weight, from about 0.25% by weight to about 10% by weight, from about 0.5% by weight to about 5% by weight, or even from about 1% by weight to about 4% by weight leuco dye.

Acid, Rosin-Based Tackifying Agent and Plasticizer

The wetness indicator composition includes a component that includes acid, rosin-based tackifying agent, plasticizer, or a combination thereof. The wetness indicator composition includes at least 10% by weight, at least 15% by weight, at least 20% by weight, from about 10% by weight to about 72% by weight, from about 15% by weight to about 65% by weight, from about 15% by weight to about 60% by weight, from about 15% by weight to about 55% by weight, from about 15% by weight to about 50% by weight, or even from about 10% by weight to about 50% by weight of the component.

Acid

The wetness indicator composition optionally includes an acid. Classes of useful acids include, e.g., organic acids, inorganic acids (e.g., hydrochloric acid, sulfuric acid, nitric acid, phosphoric acid, boric acid, and combinations thereof), and combinations thereof. Useful organic acids include, e.g., non-polymeric acids including, e.g., sulfonic acids, carboxylic acids (e.g., ascorbic, acetic, citric, formic, gluconic, lactic, oxalic, malic, maleic, tartaric, succinic, alicylic, and glycolic acids, fatty acids (e.g., stearic acid, and palmitic acid)), rosin acids (e.g., rosin acid tackifying agents); polymeric acids including, e.g., polyacrylic acids, polymethacrylic acids, and acid copolymers (e.g., copolymer that include acrylic acid, methacrylic acid, and combinations thereof); and combinations thereof.

Suitable commercially available acids are available under a variety of trade designations including, e.g., EMERSOL 132NF stearic acid from Emery Oleochemicals GmbH (Germany), AC 5120 ethylene acrylic acid from Honeywell International Inc. (Morristown, N.J.), and FORAL AX from Eastman (Kingsport, Tenn.).

The composition includes from 0% by weight to about 40% by weight, at least 2% by weight, at least 5% by weight, at least about 7% by weight, at least about 10% by weight, from about 2% by weight to about 35% by weight, from about 2% by weight to about 25% by weight, from about 2% by weight to about 20% by weight, or even from about 2% by weight to about 15% by weight acid.

Rosin-Based Tackifying Agent

The wetness indicator composition optionally includes a rosin-based tackifying agent. Useful rosin-based tackifying agents include rosin acids, rosin esters, wood rosin, tall oil rosin, gum rosin, distilled rosin, hydrogenated rosin, dimerized rosin, polymerized rosin, and combinations thereof. When a rosin acid tackifying agent is present in the composition, the rosin acid tackifying agent can function as the acid component and the rosin-based tackifying agent. Alternatively, or in addition, when a rosin acid tackifying agent is present in the composition, the composition can additionally include a second rosin-based tackifying agent different from the rosin acid tackifying agent.

Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, phenolic-modified pentaerythritol esters of rosin, and combinations thereof.

Useful commercially available rosin-based tackifying agents are available under a variety of trade designations including, e.g., the SYLVALITE series of trade designations from Arizona Chemical Company (Jacksonville, Fla.) including, e.g., SYLVALITE RE-100L, KOMOTAC KA 100L gum rosin pentaerythritol ester from Komo Pine Chemicals, Guangzhou Komo Chemical Co., Ltd. (China), the WESTREZ series of trade designations from MeadWestvaco Corp. (Richmond, Va.) including, e.g., WESTREZ 5101P and WESTREZ 5295, the FORAL series of trade designations from Eastman (Kingsport, Tenn.) including, e.g., FORAL 105-E gum rosins and FORAL AX rosin acid, and the TECKROS series of trade designations from Teckrez Inc. (Fleming Island, Fla.) including, e.g., TECKROS D85 and D95 rosin esters.

The wetness indicator composition includes from about 0% by weight to about 50% by weight, at least about 5% by weight, at least about 10% by weight, from about 5% by weight to about 50% by weight, from about 5% by weight to about 40% by weight, from about 5% by weight to about 25% by weight, or even from about 10% by weight to about 20% by weight rosin-based tackifying agent.

Plasticizer

The wetness indicator composition optionally includes a plasticizer, e.g., liquid plasticizer (i.e., a plasticizer that is liquid at room temperature), solid plasticizer, and combinations thereof. Useful liquid plasticizers include, e.g., hydrocarbon oils, mineral oil, paraffinic oil, naphthenic oil, vegetable oil, liquid esters (e.g., esters of citric acid, benzoic acid and dimer acid), and combinations thereof. Suitable commercially available liquid plasticizers are available under a variety of trade designations including, e.g., CALSOL 5550 and CALSOL 550 naphthenic oil from Calumet Specialty Products (Indianapolis, Ind.), NYFLEX 222B naphthenic oil from Nynas Napthenic AB (Sweden) and Dry #1 castor oil from Vertellus Performance Materials Inc. (Bayonne, N.J.). One example of a suitable commercially available solid plasticizer is BENZOFLEX 352, which is available from Eastman Specialties Holdings Corp. (Kingsport, Tenn.).

The composition includes from 0% by weight to about 50% by weight, at least about 2% by weight, at least about 5% by weight, at least about 10% by weight, at least about 15% by weight, from about 2% by weight to about 40% by weight, or even from about 5% by weight to about 30% by weight plasticizer.

Additional Components

The wetness indicator composition optionally includes additional components including, e.g., non-rosin-based tackifying agents, stabilizers, antioxidants, additional polymers, adhesion promoters, ultraviolet light stabilizers (e.g., TINUVIN P from BASF Corporation), rheology modifiers, biocides, corrosion inhibitors, dehydrators, colorants (e.g., pigments and dyes), fillers, surfactants, flame retardants, and combinations thereof.

Useful classes of non-rosin-based tackifying agents include, e.g., natural and synthetic terpenes, and derivatives thereof, aromatic, aliphatic and cycloaliphatic hydrocarbon resins, mixed aromatic and aliphatic modified hydrocarbon resins, aromatic modified aliphatic hydrocarbon resins, and hydrogenated versions thereof, terpenes, modified terpenes and hydrogenated versions thereof, low molecular weight polylactic acid, and combinations thereof.

Examples of useful aliphatic and cycloaliphatic petroleum hydrocarbon resins, including aliphatic and cycloaliphatic petroleum hydrocarbon resins having Ring and Ball softening points of from about 10° C. to about 140° C. (e.g., branched and unbranched C5 resins, C9 resins, and C10 resins and styrenic and hydrogenated modifications thereof), alpha-methyl styrene resins, and the hydrogenated derivatives thereof.

Examples of useful polyterpene resins include polyterpene resins having a softening point, as determined by ASTM method E28-58T, of from about 10° C. to about 140° C., hydrogenated polyterpene resins, copolymers and terpolymers of natural terpenes (e.g. styrene-terpene, alpha-methyl styrene-terpene, and vinyl toluene-terpene), and combinations thereof.

Useful tackifying agents are commercially available under a variety of trade designations including, e.g., the ESCOREZ series of trade designations from ExxonMobil Chemical Company (Houston, Tex.) including ESCOREZ 5400, ESCOREZ 5415, ESCOREZ 5600, ESCOREZ 5615, and ESCOREZ 5690, the EASTOTAC series of trade designations from Eastman Chemical (Kingsport, Tenn.) including EASTOTAC H-100R, EASTOTAC H-100L, and EASTOTAC H130W, the WINGTACK series of trade designations from Cray Valley HSC (Exton, Pa.) including WINGTACK 86, WINGTACK EXTRA and WINGTACK 95, the PICCOTAC series of trade designations from Eastman Chemical Company (Kingsport, Tenn.) including, e.g., PICCOTAC 8095, and ZONATAC NG 98 and SYLVARES ZT 105 styrenated terpene resins available from Arizona Chemical Company (Dover, Ohio).

The wetness indicator composition includes from 0% by weight to about 60% by weight, at least about 5% by weight, at least about 10% by weight, from about 5% by weight to about 60% by weight, from about 5% by weight to about 55% by weight, or even from about 5% by weight to about 50% by weight of a non-rosin-based tackifying agent.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants, and IRGAFOS 168 phosphite antioxidant, all of which are available from BASF Corporation (Florham Park, N.J.). When present, the wetness indicator composition preferably includes from about 0.02% by weight to about 2% by weight antioxidant.

Useful colorants are commercially available under a variety of trade designations including, e.g., KEYPLAST ORANGE LFP, KEYPLAST YELLOW G, KEYPLAST RED 2G, KEYPLAST GREEN B, and KEYSTONE D&C ORANGE #4 from Keystone, Inc. (Chicago, Ill.). The colorant can be used to impart a color to the wetness indicating composition (e.g., to impart a color to the wetness indicating composition as it exists prior to contact with an aqueous composition). The color imparted by the colorant can be a color that is different from the color exhibited by a protonated form of the leuco dye.

Method

One useful method of preparing the composition includes combining, with mixing and heating, the Leuco dye and the anionic surfactant, and acid, tackifying agent, or plasticizer, or a combination of any of the foregoing, until the mixture forms a molten homogeneous composition. Then the water insoluble polymer is added to the composition with mixing until the mixture forms a molten homogeneous composition. The composition is preferably prepared under an inert environment, e.g., nitrogen.

Another useful method of preparing the composition includes combining initial amounts of tackifying agent and oil, and the leuco dye, with mixing and heating until a molten homogeneous composition is formed. The water insoluble polymer (e.g., an elastomer) is then added and the composition, which is sheared until a molten homogeneous composition is formed. Surfactant is then added to the molten composition and the composition is sheared until homogeneous. Acid and residual amounts of tackifying agent and oil then are added with mixing until a molten homogeneous composition is obtained.

Uses

The wetness indicator composition can provide a color signal when the composition has been contacted with an aqueous composition (e.g., water, urine, saline, and combinations thereof), which can signal to an observer that an article (e.g., a diaper) with which the wetness indicator composition is associated has been in contact with an aqueous composition (e.g., water, urine, saline, and combinations thereof). The wetness indicator composition is useful in a variety of forms including, e.g., as a coating (e.g., continuous coatings and discontinuous (e.g., random, pattern, and array) coatings), a film (e.g., continuous films and discontinuous films), and as fibers. The wetness indicator composition can be applied on or incorporated in a variety of substrates including, e.g., films (e.g., polyolefin (e.g., polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers), tape backings, components of absorbent articles including, e.g., absorbent elements, absorbent cores, impermeable layers (e.g., back sheets (e.g., polyolefin film back sheets)), tissue (e.g., wrapping tissue), acquisition layers and woven and nonwoven web layers (e.g., top sheets, absorbent tissue), labels, tapes, and combinations thereof.

The wetness indicator composition is also useful as a component in a variety of applications and in or on a variety of constructions including, e.g., disposable absorbent articles including, e.g., disposable diapers (e.g., adult incontinence diapers), training pants, incontinence pads, sanitary napkins, medical dressings (e.g., wound care products) bandages, surgical pads, drapes, gowns, and meat-packing products, paper products including, e.g., paper towels (e.g., multiple use towels), toilet paper, facial tissue, wipes, tissues, and towels (e.g., paper towels), sheets, mattress covers, packaging materials (e.g., boxes, cartons, trays, and bags (e.g., paper and polymeric)), and combinations thereof.

Various techniques for applying hot melt compositions can be used to apply the hot melt wetness indicator composition to a substrate including, e.g., intermittent coating, continuous coating, slot coating, spraying including, e.g., spiral spraying and random spraying, screen printing, foaming, roller coating, engraved roller coating, wheel coating, extrusion (e.g., applying a bead, fine line extrusion, single screw extrusion, and twin screw extrusion), meltblown, noncontact coating, contacting coating, transfer coating, screen printing, flexographic, "on demand" application techniques, and combinations thereof.

In on demand hot melt application systems (which are also referred to as "tank free" and "tankless" systems), hot melt compositions are fed in a solid state (e.g., pellets), to a relatively small heating vessel (relative to traditional hot melt applications systems that include a pot) where the hot melt composition is melted and, typically shortly thereafter, the molten liquid is applied to a substrate. In many existing on demand systems, the volume of molten hot melt composition is no greater than about 1 liter, or even no greater than about 500 milliliters, and the hot melt composition is maintained in a molten state for a relatively brief period of time, including, e.g., less than two hours, less than one hour, or even less than 30 minutes. Suitable on demand hot melt adhesive application systems include, e.g., InvisiPac Tank-Free Hot Melt Delivery System from Graco Minnesota Inc. (Minneapolis, Minn.) and the Freedom Hot Melt Dispensing System from Nordson Corporation (Westlake, Ohio). On demand hot melt adhesive application systems are described in U.S. Patent Publication Nos. 2013-0105039, 2013-0112709, 2013-0112279, and 2014-0042182, and U.S. Pat. No. 8,201,717, and incorporated herein.

The hot melt wetness indicator composition can be applied at temperatures greater than the softening point of the composition. The application temperature of the hot melt wetness indicator composition preferably is at least 10° C. greater than, at least 15° C. greater than, or even at least 20° C. greater than the softening point of the composition. Useful application temperatures include, e.g., at least about 90° C., at least about 100° C., no greater than about 180° C., from about 90° C. to about 150° C., from about 100° C. to about 140° C., or even from about 100° C. to about 130° C.

The invention will now be described by way of the following examples. All parts, ratios, percentages and amounts stated in the Examples are by weight unless otherwise specified.

EXAMPLES

Test Procedures

Test procedures used in the examples include the following. All ratios and percentages are by weight unless otherwise indicated. The procedures are conducted at room temperature (i.e., an ambient temperature of from about 20° C. to about 25° C.) unless otherwise specified.

Viscosity Test Method

Viscosity is determined in accordance with ASTM D-3236 entitled, "Standard Test Method for Apparent viscosity of Hot Melt Adhesives and Coating Materials," (Oct. 31, 1988), using a Brookfield Thermosel viscometer Model RVDV 2, and a number 27 spindle. The results are reported in centipoise (cP). The viscosity of the wetness indicator composition is measured at 110° C.

Laminate Preparation Method

The laminate is prepared by coating the sample onto a polyethylene film using an ITW slot applicator to provide a 4 mm wide pattern of composition at an add-on weight of 50 grams per square meter (g/m$^2$). The polyethylene film is a 1 mil thick white, non-breathable polyethylene film that has been corona treated to a surface energy of 38 dynes/cm (an example of which is CLOPAY DH-284 PE film), and the sample is coated on the corona treated side of the polyethylene film. A spunbond polypropylene non-woven material having a basis weight of approximately 15 g/m$^2$ is then laminated to the exposed surface of the coated composition to form a laminate. Test strips are created by cutting 10 centimeter (cm) samples from the laminate in the machine direction of the laminate.

Color Change Test Method

A laminate test strip is prepared according to the Laminate Preparation Method. Twenty-four hours after the laminate test strip has been prepared, the test strip is placed on white printer paper with the polyethylene film facing up, and the initial color of the test strip is observed through the film and the color is recorded. The test strip is then turned over to expose the nonwoven side of the laminate, and then the test strip is insulted by adding approximately 2 mL of saline solution (i.e., a solution of approximately 0.9% sodium chloride in distilled water) to the wetness indicator portion of the test strip through the nonwoven side of the laminate. After insult, the time to achieve final color is measured. The final color of the test strip is then observed through the polyethylene film side of the test strip and the results are recorded. Two test strips are tested for each composition and the average result is recorded.

Humidity Resistance Test Method

Commercially available diaper cores are cut into 15 cm×15 cm size pieces. A diaper prototype is prepared by removing a 1 cm×15 cm strip of the back sheet of the diaper core. The test strips prepared according to the Laminate Preparation Method are then placed on the diaper prototype such that the nonwoven surface of the laminate is in contact with the core material. The test strip is held in place and all sides of the test strip are sealed in place against the back sheet using a clear packaging tape such as Scotch Brand 373. The resulting prototype diaper is then placed in a humidity chamber maintained at 40° C. and 75% Relative Humidity. After aging for a specified period of time, the prototype diaper is removed from the chamber and the color of the test strip is observed through the polyethylene film. Two test strips are tested for each composition and the average of the color observations is recorded.

Thermal Stability Test Method

A 50 g sample of a wetness indicator composition is placed in a 100 milliliter (mL) glass beaker, which is then placed in an oven at 110° C. After aging for a specified period of time, the samples are checked for phase separation and for the presence of solids at the bottom of the beaker. If phase separation occurs (e.g., liquid phase separation or visible particles), then the composition is deemed to lack homogeneity. If there is no phase separation, then the composition is deemed to be homogeneous.

Controls 1-3 and Examples 1-18

Controls 1-3 and Examples 1-18 were prepared as follows using the components and amounts thereof set forth in Tables 1-3. A sigma-blade mixer was set to a temperature of 177° C. in the presence of nitrogen. A portion of the tackifier and the oil and all of the acid, surfactant, and leuco dye were added to the mixer and mixed until all of the components were melted and formed a composition that was homogeneous and free of bubbles. Polymer and the residual amounts of tackifier and oil were then added to the composition and the composition was sheared until a homogeneous composition was obtained with the exception that the compositions of Controls 1-3 were not homogeneous.

Control 4 and Example 19

The compositions of Control 4 and Example 19 were prepared according to the method used in Example 1 with the exception that the composition was prepared in an upright mixer instead of a sigma-blade mixer and was mixed using a stir bar. The composition of Control 4 was not homogeneous Example 20

Example 20 was prepared as follows using the components and amounts thereof set forth in Table 3. A sigma-blade mixer was set to a temperature of 177° C. in the presence of nitrogen. Partial amounts of tackifier and oil and the total amount of leuco dye were then added to the mixer and mixed until all of the components formed a homogeneous composition. Polymer was then added to the composition and the composition was sheared until all of the components formed a homogeneous composition. Surfactant was then added to the composition and the composition was sheared until homogeneous. Then, the acid and the residual amounts of tackifier and oil were added to the composition with mixing until a homogeneous composition was obtained.

The compositions of Controls 1-4 and Examples 1-20 were tested according to the Viscosity, Color Change, Humidity Resistance, and Thermal Stability test methods. The results are set forth in Tables 1-3 below. For the Humidity Resistance test, the samples were aged for approximately 24 hours. For the thermal stability test, the samples were aged for 72 hours.

TABLE 1

| Control | 1 | 2 | 3 | 4 |
|---|---|---|---|---|
| KRATON G 1652 | 13.16 | 0 | 0 | 0 |
| ESCORENE AD2528 | 0 | 56.2 | 58 | 0 |
| ATEVA 2850 | 0 | 0 | 0 | 68.2 |
| ESCOREZ 5400 | 26.31 | 0 | 0 | 0 |
| CALSOL 550 | 38.5 | 18.8 | 22 | 22.7 |
| RHODACAL DS-10 | 17.05 | 15.6 | 10 | 5.1 |
| Leuco Dye 1 | 2.44 | 3.1 | 4 | 0 |
| Leuco Dye 2 | 0 | 0 | 0 | 4 |
| EMERSOL 132 | 2.54 | 6.3 | 6 | 0 |
| Initially Homogeneous? | No | No | No | No |
| Thermal Stability | Visible solids settling in the composition | Visible solids settling in the composition | Visible solids settling in the composition | Visible solids settling in the composition |
| Observations | Particles caused machining problems. | Particles caused machining problems. | Particles caused machining problems. | Particles caused machining problems. |

KRATON G 1652 = Styrene-ethylene/butylene-styrene block copolymer (Kraton Polymers LLC, Houston, Texas)
ESCORENE AD2528 = ethylene vinyl acetate copolymer (ExxonMobil Chemical Company, Houston, Texas)
ATEVA 2850 = ethylene vinyl acetate copolymer
ESCOREZ 5400 = Cycloaliphatic hydrocarbon resin (ExxonMobil Chemical Company, Houston, Texas)
CALSOL 550 = naphthenic oil (Calumet Specialty Products, Indianapolis, Indiana)
RHODACAL DS-10 = sodium dodecylbenzene sulfonate (Solvay Americas, Inc., Houston, Texas)
Leuco Dye 1 = Crystal Violet Lactone (Shanghai Lucky B&C Technology Co. Ltd., Shanghai, China)
Leuco Dye 2 = N-102 (Esco Co. LLC, Muskegon, Michigan)
EMERSOL 132NF stearic acid (Emery Oleochemicals GmbH, Germany)

TABLE 2

| Example | 1 | 2 | 3 | 4 | 5 | 6 | 7 | 8 |
|---|---|---|---|---|---|---|---|---|
| Polymer 1 | 53.1 | 61.0 | 44.8 | 47.3 | 47.3 | 42.8 | 45 | 43.7 |
| Polymer 2 | 0 | 0 | 0 | 0 | 0 | 0 | 0 | 0 |
| Polymer 3 | 0 | 0 | 0 | 0 | 0 | 0 | 0 | 0 |
| Polymer 4 | 0 | 0 | 0 | 0 | 0 | 0 | 0 | 0 |
| Polymer 5 | 0 | 0 | 0 | 0 | 0 | 0 | 0 | 0 |
| Polymer 6 | 0 | 0 | 0 | 0 | 0 | 0 | 0 | 0 |
| Plasticizer 1 | 18.8 | 0 | 22.4 | 22.4 | 22.4 | 16.9 | 20 | 21.8 |
| Plasticizer 2 | 0 | 20.3 | 0 | 0 | 0 | 0 | 0 | 0 |
| Surfactant | 9.4 | 6.8 | 12.4 | 9.0 | 6.5 | 12.4 | 10.0 | 13.9 |
| Leuco Dye 1 | 3.1 | 1.7 | 2.5 | 2.5 | 2.5 | 2.5 | 2.5 | 2.5 |
| Leuco Dye 3 | 0 | 0 | 0 | 0 | 0 | 0 | 0 | 0 |
| Acid 1 | 6.2 | 10.2 | 5 | 7.5 | 10.9 | 3.0 | 4.5 | 0 |
| Acid 2 | 0 | 0 | 0 | 0 | 0 | 0 | 0 | 7.5 |
| Acid 3 | 0 | 0 | 0 | 0 | 0 | 0 | 0 | 0 |
| Tackifier 1 | 9.4 | 0 | 12.4 | 10.9 | 10.0 | 21.9 | 18.0 | 9.9 |
| Tackifier 2 | 0 | 0 | 0 | 0 | 0 | 0 | 0 | 0 |
| Tackifier 3 | 0 | 0 | 0 | 0 | 0 | 0 | 0 | 0 |
| UV Stabilizer | 0 | 0 | 0 | 0 | 0 | 0 | 0 | 0.2 |
| Antioxidant | 0 | 0 | 0.5 | 0.5 | 0.5 | 0.5 | 0.0 | 0.5 |
| Viscosity at 110° C. | 9450 | 14850 | 6363 | 6012 | 5025 | 7875 | 5725 | 6950 |
| Initially Homogeneous? | Yes | Yes | Yes | Yes | Yes | Yes | Yes | Yes |

TABLE 2-continued

| Color Change | | | | | | | | |
|---|---|---|---|---|---|---|---|---|
| Initial Color | Light green | Light green | Unnoticeable | Very light green | Light green | Unnoticeable | Very light green | Unnoticeable |
| Time to change (min) | <1 | <5 | <1 | <1 | <1 | <3 | <1 | <1 |
| Final Color | Dark, bright blue | Bright blue | Deep dark blue | Deep dark blue | Bright blue | Bright blue | Bright blue | Bright blue |
| Humidity Resistance | ND | ND | No change | No change | No change | Light change | No change | No change |
| Thermal Stability | ND | ND | H | H | H | H | H | H |

| Example | 9 | 10 | 11 | 12 | 13 | 14 | 15 |
|---|---|---|---|---|---|---|---|
| Polymer 1 | 0 | 37.5 | 0 | 0 | 0 | 0 | 0 |
| Polymer 2 | 55.6 | 0 | 0 | 0 | 0 | 0 | 0 |
| Polymer 3 | 0 | 0 | 15 | 14.9 | 15 | 15 | 14 |
| Polymer 4 | 0 | 0 | 0 | 0 | 0 | 0 | 0 |
| Polymer 5 | 0 | 0 | 0 | 0 | 0 | 0 | 0 |
| Polymer 6 | 0 | 0 | 0 | 0 | 0 | 0 | 0 |
| Plasticizer 1 | 12.4 | 18.8 | 25 | 24.9 | 21 | 27.9 | 20 |
| Plasticizer 2 | 0 | 0 | 0 | 0 | 0 | 0 | 0 |
| Surfactant | 12.4 | 9.4 | 13 | 12.9 | 14 | 8 | 13 |
| Leuco Dye 1 | 2.5 | 3.1 | 3 | 3 | 2 | 1 | 2 |
| Leuco Dye 3 | 0 | 0 | 0 | 0.4 | 0 | 0 | 0 |
| Acid 1 | 4.0 | 6.3 | 0 | 0 | 6 | 8 | 20 |
| Acid 2 | 0 | 0 | 0 | 0 | 0 | 0 | 0 |
| Acid 3 | 0 | 25 | 0 | 0 | 0 | 0 | 0 |
| Tackifier 1 | 12.4 | 0 | 15 | 14.9 | 10 | 5 | 30.9 |
| Tackifier 2 | 0 | 0 | 0 | 0 | 31.9 | 34.9 | 0 |
| Tackifier 3 | 0 | 0 | 28.9 | 28.8 | 0 | 0 | 0 |
| UV Stabilizer | 0.2 | 0 | 0 | 0 | 0 | 0 | 0 |
| Antioxidant | 0.5 | 0 | 0.2 | 0.2 | 0.2 | 0.2 | 0.2 |
| Viscosity at 110° C. | ND | ND | 23100 | 23100 | 6500 | 5925 | 3394 |
| Initially Homogeneous? | Yes | Yes | Yes | Yes | Yes | Yes | Yes |
| Color Change | | | | | | | |
| Initial Color | Light green | Light green | Very light blue | Light grey | Light blue | Very light blue | Light blue |
| Time to change (min) | <1 | <1 | <3 | <5 | <1 | <5 | <1 |
| Final Color | Deep Bright blue | Deep Bright blue | Light blue | Deep dark blue | Bright blue | Light blue | Bright blue |
| Humidity Resistance | No change | ND | ND | No change | No change | No change | Light change |
| Thermal Stability | H | Visible liquid phase separation | Visible liquid phase separation | Visible liquid phase separation | H | H | H |

Leuco Dye 1 = Crystal Violet Lactone (Shanghai Lucky B&C Technology Co. Ltd., Shanghai, China)
Leuco Dye 3 = Blue 230 (Nagase Inc., japan)
Polymer 1 = ATEVA 2850 ethylene vinyl acetate copolymer
Polymer 2 = ESCORENE AD2528 ethylene vinyl acetate copolymer
Polymer 3 = KRATON G 1652 styrene-ethylene/butylene-styrene block copolymer
Polymer 4 = VISTAMAXX 8880 propylene/ethylene copolymer (ExxonMobil Chemical Company, Irving, Texas)
Polymer 5 = SOLPRENE 411 styrene-butadiene-styrene block copolymer
Polymer 6 = VECTOR 6241A styrene-butadiene-styrene block copolymer (TSRC/Dexco Investment Corp., Houston, Texas)
Plasticizer 1 = CALSOL 550 naphthenic oil (Calumet Specialty Products, Indianapolis, Indiana)
Plasticizer 2 = Dry #1 castor oil (Vertellus Performance Materials Inc., Bayonne, New Jersey)
Surfactant = RHODACAL DS-10 = sodium dodecylbenzene sulfonate
Acid 1 = EMERSOL 132NF stearic acid
Acid 2 = FORAL AX rosin acid
Acid 3 = AC 5120 ethylene acrylic acid (Honeywell International Inc., Morristown, New Jersey)
Tackifier 1 = SYLVALITE RE-100L rosin ester (Arizona Chemical Company, Florida)
Tackifier 2 = ESCOREZ 5400 cycloaliphatic hydrocarbon resin
Tackifier 3 = ESCOREZ 5600 aromatic modified, cycloaliphatic hydrocarbon resin (ExxonMobil Chemical Company, Houston, Texas)
UV stabilizer = TINUVIN P (BASF Corporation)
Antioxidant = IRGANOX 1010
H = homogeneous
ND = Not Determined

TABLE 3

| | 16 | 17 | 18 | 19 | 20 |
|---|---|---|---|---|---|
| Polymer 1 | 0 | 0 | 0 | 0 | 0 |
| Polymer 2 | 0 | 0 | 0 | 0 | 0 |
| Polymer 3 | 12 | 14 | 10 | 0 | 0 |
| Polymer 4 | 0 | 0 | 0 | 47 | |
| Polymer 5 | 0 | 0 | 0 | 0 | 4 |
| Polymer 6 | 0 | 0 | 0 | 0 | 8 |
| Polymer 7 | 0 | 0 | 4 | 0 | 0 |
| Plasticizer 1 | 26 | 26 | 24.9 | 10 | 25 |
| Plasticizer 2 | 0 | 0 | 0 | 0 | 0 |
| Surfactant 1 | 5 | 13 | 0 | 13 | 13 |
| Surfactant 2 | 0 | 0 | 13 | 0 | 0 |
| Leuco Dye 1 | 2 | 2.5 | 2.5 | 2 | 2.5 |
| Acid 1 | 25 | 0 | 0 | 27.8 | 6 |
| Acid 2 | 0 | 5 | 5 | 0 | 0 |
| Acid 3 | 0 | 0 | 0 | 0 | 0 |
| Tackifier 1 | 10 | 15 | 15 | 0 | 15 |
| Tackifier 2 | 20 | 0 | 0 | 0 | 26.3 |
| Tackifier 3 | 0 | 24.3 | 25.4 | 0 | 0 |
| Antioxidant | 0 | 0.2 | 0.2 | 0.2 | 0.2 |
| UV Stabilizer | 0 | 0 | 0.1 | 0 | 0 |
| Viscosity at 110° C. | 1850 | 16950 | 20650 | 1260 | 2455 |
| Initially Homogeneous? | Yes | Yes | Yes | Yes | Yes |
| Color Change | | | | | |
| Initial Color | Light blue | Light blue | Light blue | Light green | Light blue |
| Time to change (min) | <5 | <1 | <3 | <1 | <5 |
| Final Color | Blue | Dark, bright blue | Dark, bright blue | Bright blue | Blue |
| Humidity Resistance | No Change | No change | ND | Light change | No Change |
| Thermal Stability | H | H | H | H | H |

Polymer 7 = KRATON G 1650 styrene-ethylene/butylene-styrene block copolymer (Kraton Polymers LLC, Houston, Texas)

Examples 21-24

Examples 21-23 were prepared as follows using the components and amounts thereof set forth in Table 4. A sigma-blade mixer was set to a temperature of 177° C. in the presence of nitrogen. A partial amount of the tackifier and all of the acid, oil, leuco dye, antioxidant, and UV stabilizer were added to the mixer and mixed until all of the components formed a homogeneous composition. Surfactant was then added to the mixer and mixed until homogeneous. Polymer and the residual amount of tackifier was then added to the composition and the composition was sheared until all of the components formed a homogeneous composition. For Example 22, the yellow dye was added to the composition and mixed until homogeneous using an upright mixer set at 300° F.

Example 24 was prepared as follows using the components and amounts thereof set forth in Table 4. A sigma-blade mixer was set to a temperature of 177° C. in the presence of nitrogen. Partial amounts of tackifier and oil, and all of the acid, leuco dye, and antioxidant were added to the mixer and mixed until all of the components formed a homogeneous composition. Then the surfactant was added to the mixer and the composition was mixed until homogeneous. Polymer and the residual amount of tackifier and oil was then added to the composition and the composition was sheared until all of the components formed a homogeneous composition.

The compositions of Examples 21-24 were tested according to the Viscosity, Color Change, Humidity Resistance, and Thermal Stability test methods. The results are set forth in Table 4 below. For the Humidity Resistance test, the samples were aged for approximately 24 hours. For the thermal stability test, the samples were aged for 72 hours.

TABLE 4

| Example | 21 | 22 | 23 | 24 |
|---|---|---|---|---|
| ESCORENE AD2528 | 50 | 50 | 50 | 0 |
| SYLVALITE RE 100L | 12 | 12 | 0 | 5 |
| KRATON 1652 | 0 | 0 | 0 | 12 |
| CALSOL 550 | 14 | 13.97 | 14 | 27 |
| RHODICAL DS-10 | 13 | 13 | 13 | 0 |
| NACCONOL 90G | 0 | 0 | 0 | 15 |
| ESCOREZ 5600 | 0 | 0 | 15 | 25.3 |
| Crystal Violet Lactone | 2.5 | 2.5 | 2.5 | 2.5 |
| FORAL AX | 3 | 3 | 0 | 8 |
| EMERSOL 132NF | 5 | 5 | 5 | 0 |
| WESTREZ 5295 | 0 | 0 | 0 | 5 |
| IRGANOX 1010 | 0.3 | 0.3 | 0.3 | 0 |
| TINUVIN P | 0.2 | 0.2 | 0.2 | 0.2 |
| KEYPLAST ORANGE | | 0.03 | 0 | 0 |
| Total | 100 | 100 | 100 | 100 |
| Viscosity at 110° C. | 4,575 | 4,587 | 4,600 | 2875* |
| Initially Homogeneous | Yes | Yes | Yes | Yes |
| Initial Color | Unnoticeable | Yellow | Unnoticeable | Unnoticeable |
| Time to Change | <1 min | <1 min | <1 min | <1 min |
| Final Color | Bright Blue | Dark Blue | Bright Blue | Bright Blue |
| Humidity Resistance | No change | No change | No change | No change |
| Thermal Stability | H | H | H | H |

*The viscosity of Example 24 was determined at 250° F.

NACCONOL 90G = sodium dodecylbenzene sulfonate (Stepan Company, Northfield, Illinois)

WESTREZ 5295 = modified rosin resin (MeadWestvaco Corp., Richmond, Virginia)

KEYPLAST ORANGE = dye (Keystone, Inc., Chicago, Illinois)

Other embodiments are within the claims.

What is claimed is:

1. A hot melt wetness indicator composition comprising:
at least 5% by weight water insoluble thermoplastic polymer;
at least 3% by weight anionic surfactant;
leuco dye; and
at least 10% by weight of a component selected from the group consisting of acid, rosin-based tackifying agent, plasticizer, and combinations thereof, the component being other than the anionic surfactant and the thermoplastic polymer,
the hot melt wetness indicator composition being homogeneous and exhibiting a color change after contact with water.

2. The wetness indicator composition of claim 1, wherein the composition comprises at least 5% by weight rosin-based tackifying agent.

3. The wetness indicator composition of claim 1, wherein the composition comprises from about 10% by weight to no greater than 60% by weight rosin-based tackifying agent.

4. The wetness indicator composition of claim 1, wherein the composition comprises at least 2% by weight acid.

5. The wetness indicator composition of claim 1, wherein the composition comprises at least 2% by weight rosin acid.

6. The wetness indicator composition of claim 1, wherein the composition comprises at least 5% by weight plasticizer.

7. The wetness indicator composition of claim 1, wherein the composition comprises at least two components selected from the group consisting of acid, rosin-based tackifying agent, and plasticizer, the rosin-based tackifying agent being different from the acid.

8. The wetness indicator composition of claim 1, wherein the composition comprises at least about 15% by weight rosin-based tackifying agent, plasticizer, or a combination thereof.

9. The wetness indicator composition of claim 1, wherein the composition comprises at least about 15% by weight plasticizer, acid, or a combination thereof.

10. The wetness indicator composition of claim 1, wherein the composition comprises acid, plasticizer, and rosin-based tackifying agent, the rosin-based tackifying agent being different from the acid.

11. The wetness indicator composition of claim 1, wherein the composition comprises from about 10% by weight to no greater than 90% by weight of the water insoluble thermoplastic polymer.

12. The wetness indicator composition of claim 1, wherein the composition comprises from about 10% by weight to no greater than 65% by weight of the water insoluble thermoplastic polymer.

13. The wetness indicator composition of claim 1, wherein the composition exhibits a viscosity of from about 1000 cP to no greater than about 20,000 cP at 110° C.

14. The wetness indicator composition of claim 1, wherein the composition comprises from about 5% by weight to no greater than about 30% by weight anionic surfactant.

15. The wetness indicator composition of claim 1, wherein the composition remains homogeneous when maintained at 110° C. for 1 day.

16. The wetness indicator composition of claim 1, wherein the composition remains homogeneous when maintained at 110° C. for 2 days.

17. The wetness indicator composition of claim 1 further comprising a colorant other than the leuco dye.

18. The wetness indicator composition of claim 17, wherein the composition exhibits a blue color when contacted with water.

19. A disposable absorbent article comprising:

a first substrate; and the hot melt wetness indicator composition of claim 1 disposed on the first substrate.

* * * * *